US00PP29352P2

(12) United States Plant Patent
Zaiger et al.

(10) Patent No.: US PP29,352 P2
(45) Date of Patent: Jun. 5, 2018

(54) PEACH TREE NAMED 'SNOW BELLE'

(50) Latin Name: *Prunus persica*
Varietal Denomination: Snow Belle

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 66 days.

(21) Appl. No.: 15/330,725

(22) Filed: Nov. 1, 2016

(51) Int. Cl.
*A01H 5/12* (2018.01)
*A01H 5/08* (2018.01)

(52) U.S. Cl.
USPC ..... Plt./195
CPC ..... *A01H 5/0868* (2013.01)

(58) Field of Classification Search
USPC ..... Plt./195
See application file for complete search history.

*Primary Examiner* — Anne Marie Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Fruit having firm, white flesh with a very good flavor and eating quality.
4. Fruit having an attractive red skin color.
5. Fruit with good storage and shipping qualities.

1 Drawing Sheet

Botanical designation: *Prunus persica.*
Variety denomination: 'Snow Belle'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Super Lady' Peach (U.S. Plant Pat. No. 15,578) and 'Snow Fox' Peach (U.S. Plant Pat. No. 27,790).

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as an open pollinated seedling originating from seed collected from 'Snow Fox' Peach (U.S. Plant patent application Ser. No. 14/544,568). A large group of these open pollinated seedlings were budded to older established trees of 'Nemaguard' Rootstock (non-patented) to enhance earlier fruit production. Under close and careful observation the present budded seedling exhibited desirable fruit and tree characteristics and was selected in 2009 for additional asexual propagation and commercialization.

ASEXUAL REPRODUCTION OF THE VARIETY

In 2009 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of large size, white flesh, clingstone fruit. The fruit is further characterized by its moderately juicy, firm flesh and having an attractive red skin color. In comparison to its seed parent 'Snow Fox' Peach (U.S. Plant patent application Ser. No. 14/544,568) the fruit of the new variety is approximately 3 weeks earlier in maturity. In comparison to the commercial variety 'Super Lady' Peach (U.S. Plant Pat. No. 15,578) the fruit of the new variety has white flesh compared to yellow and is larger in size.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility and climatic conditions.

*Form*.—Upright, usually pruned to vase shape.

*Branching habit*.—Upright, crotch angle approximately 25°, increases with heavy crop load.

*Productivity*.—Productive, thinning and spacing of fruit desirable for marketable size. Fruit set varies with climatic conditions during bloom time.

*Bearer*.—Regular, has had adequate fruit set 6 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 300 hours at or below 45° F.

Trunk:

*Size*.—Large. Average circumference 49.5 cm at 20.3 cm above ground on a 7 year old tree.

*Stocky*.—Medium stocky.

*Texture*.—Medium shaggy, roughness increases with age.

*Color*.—Varies from 10YR 4/2 to 10YR 3/2.

Branches:

*Size*.—Medium. Average circumference 20.0 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 22 in a 25.8 square cm area. Average length 7.8 mm. Average width 2.8 mm. Color varies from 2.5Y 6/8 to 2.5Y 5/8.

*Color*.—New growth varies from 5GY 7/6 to 5GY 6/6. Mature growth varies from 7.5YR 4/2 to 7.5YR 2/2, varies with age of growth.

Leaves:

*Size*.—Large. Average length 116.5 mm. Average width 36.7 mm.

*Form*.—Elliptical.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.8 mm. Average width 1.5 mm. Longitudinally grooved. Surface — glabrous. Color varies from 5GY 6/6 to 5GY 5/6.

*Glands*.—Type — reniform. Size — Average length 1.3 mm. Average width 0.9 mm. Number varies from 1 to 3, average number 2. Located primarily on the base of the leaf blade and upper portion of the petiole. Color varies from 10R 3/4 to 7.5R 2/4.

*Stipules*.—None present at time of measurement.

*Color*.—Upper surface varies from 2.5GY 4/4 to 2.5GY 4/6. Lower surface varies from 2.5GY 5/4 to 2.5GY 5/6. Midvein color varies from 7.5Y 8.5/4 to 10Y 8.5/4.

Flower buds:

*Size*.—Large. Average length 20.6 mm. Average diameter 12.2 mm.

*Hardiness*.—Hardy with respect to California winters.

*Density*.—Medium dense.

*Form*.—Conical, becoming elongated just before opening.

*Pedicel*.—Average length 5.4 mm. Average width 1.2 mm. Surface — glabrous. Color varies from 5GY 6/8 to 2.R 2/4.

*Color*.—Varies from 5RP 8/6 to 5RP 7/8.

Flowers:

*Blooming period*.—Date of First Bloom Feb. 3, 2016. Date of Petal Fall Feb. 10, 2016, varies slightly with climatic conditions.

*Size*.—Large. Average height 21.3 mm. Average diameter 42.7 mm.

*Petals*.—Normally 5, alternately arranged to sepals. Size — large. Average length 19.9 mm. Average width 19.7 mm. Form — obovate. Petal apex — rounded. Petal base — truncate. Margin — sinuate. Arrangement — free. Both upper and lower surfaces glabrous. Color varies from 5RP 8/4 to 7.5RP 8/4, fades with age of flower.

*Sepals*.—Normally 5, alternately arranged to petals. Size — large. Average length 6.0 mm. Average width 5.5 mm. Shape — ovate, apex rounded to triangular. Margin — entire. Surface — upper surface glabrous, lower surface pubescent. Color — upper surface varies from 5GY 5/6 to 7.5R 3/6. Lower surface 5R 2/4.

*Stamens*.—Average number per flower 45. On average, the stamens are above the height of the petals. Filament color varies from N 9.5/(white) to 5RP 6/8, depending on age of flower. Anther color varies from 7.5R 3/12 to 5Y 8/8.

*Pollen*.—Self fertile. Color varies from 5Y 8/8 to 5Y 7/8.

*Pistil*.—Number — normally 1. Average length 19.6 mm. Position of stigma an average of 1.7 below anthers. Surface — pubescent. Color varies from 10Y 8/4 to 2.5GY 8/6.

*Fragrance*.—Heavy.

*Color*.—Varies from 2.5RP 8/4 to 5RP 7/6.

*Pedicel*.—Average length 4.9 mm. Average width 1.3 mm. Color varies from 5GY 5/6 to 2.5R 2/4.

*Number flowers per flower bud*.—Normally one.

Fruit:

*Maturity when described*.—Firm ripe and ready for consumption.

*Date of first picking*.—May 9, 2016.

*Date of last picking*.—May 19, 2016, varies slightly with climatic conditions.

*Size*.—Large. Average diameter axially 70.7 mm. Average transversely in suture plane 81.1 mm. Average weight 258.4 grams, varies slightly with fertility of the soil, amount of thinning and climatic conditions.

*Form*.—Globose.

*Suture*.—Nearly smooth.

*Ventral surface*.—Nearly smooth.

*Apex*.—Slightly retuse.

*Base*.—Retuse.

*Stem cavity*.—Rounded to slightly elongated in suture plane. Average depth 12.9 mm. Average diameter 9.7 mm.

Stem:

*Size*.—Medium. Average length 11.0 mm. Average diameter 3.2 mm.

*Color*.—Varies from 2.5GY 6/8 to 5GY 5/6.

Flesh:

*Ripens*.—Evenly, some fruit slightly earlier at the apex.

*Texture*.—Firm, meaty, crisp.

*Fibers*.—Few, small, tender.

*Firmness*.—Firm, comparable to other commercial peach varieties.

*Aroma*.—Moderate.

*Amydgalin*.—Undetected.

*Eating quality*.—Very good.

*Flavor*.—Very good, with a good balance between acid and sugar.

*Juice*.—Moderate amount, enhances flavor.

*Acidity*.—Not available.

*Brix*.—Average Brix 10.0°, varies slightly with amount of fruit per tree and climatic conditions.

*Color*.—Varies from 2.5Y 9/2 to 5Y 9/2 with 2.5R 4/10 anthocyanin color near edges.

*Pit cavity*.—Average length 33.4 mm. Average width 26.9 mm. Average depth 11.7 mm. Color varies from 5Y 8/4 to 7.5Y 8/4.

Skin:

*Thickness*.—Medium.

*Surface*.—Smooth.

*Pubescence*.—Moderate amount, short in length.

*Tendency to crack*.—None.

*Color*.—Ground color varies from 5Y 8.5/2 to 7.5Y 9/2. Overspread with 7.5R 4/8 to 7.5R 3/10.

*Tenacity*.—Tenacious to the flesh.

*Astringency*.—Undetected.

Stone:

*Type*.—Clingstone, strong adherence to flesh.

*Size*.—Large. Average length 32.4 mm. Average width 25.9 mm. Average thickness 21.4 mm.

*Form*.—Ovoid.

*Base*.—Flat.

*Apex*.—Pointed. Average length 1.2 mm.

*Surface*.—Pitted throughout, pits vary from rounded to slightly elongated.

*Sides*.—Unequal, one side extending further from suture plane.

*Ridges*.—Relatively smooth, narrow ridges extending from base toward apex.

*Tendency to split*.—None.

*Color*.—Varies from 5YR 5/6 to 7.5YR 6/6 when dry.

Kernel:

*Size*.—Large. Average length 17.5 mm. Average width 11.9 mm. Average depth 7.0 mm.

*Form*.—Ovate.

*Viability*.—Partially viable, some embryos with incomplete development.

*Skin color*.—Varies from 5Y 9/4 to 7.5Y 9/4.

Use:

*Dessert*.—Market — local and long distance.

Keeping quality: Good, held firm in cold storage for 2 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

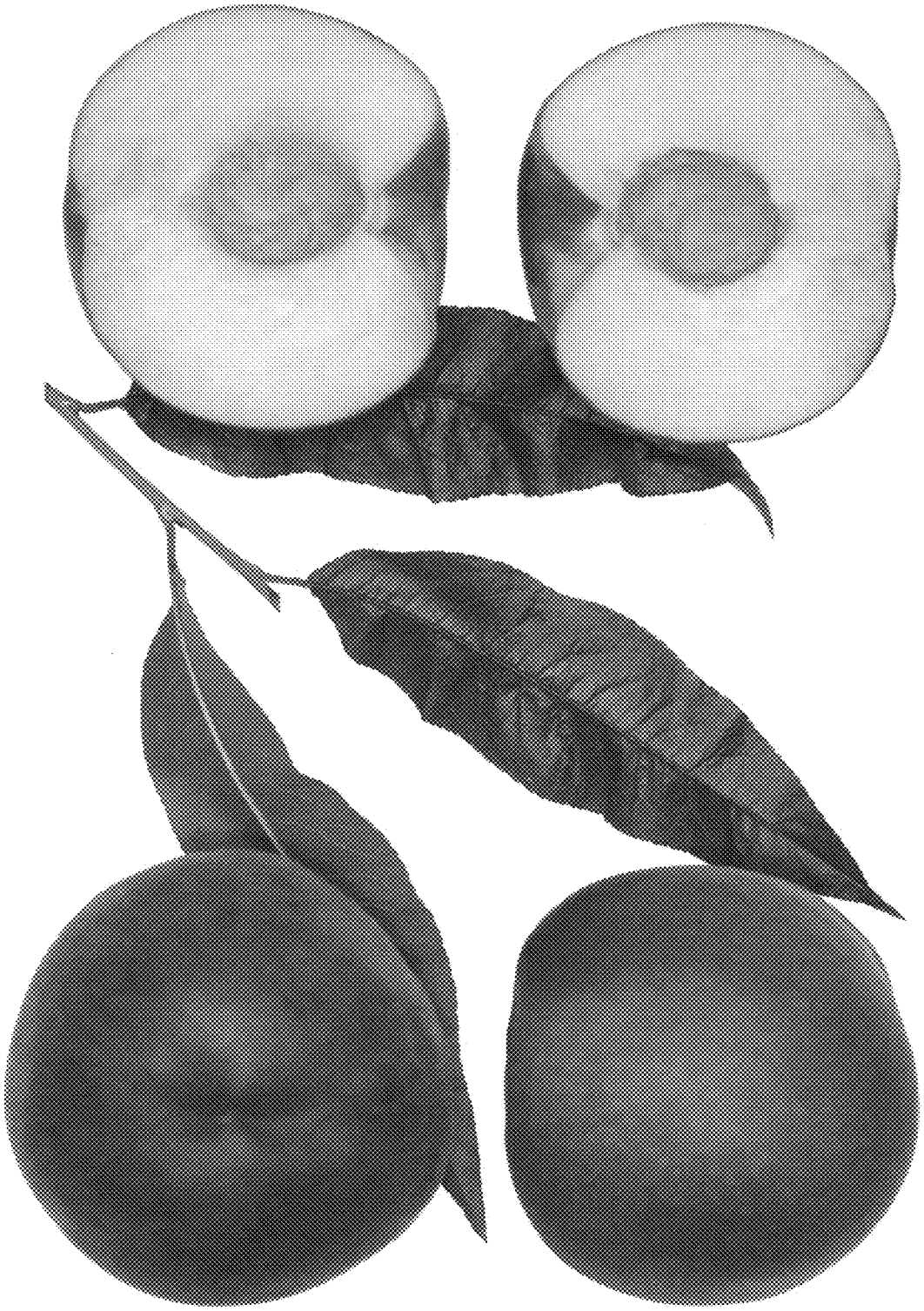

* * * * *